(12) United States Patent
Rose

(10) Patent No.: US 6,328,565 B1
(45) Date of Patent: Dec. 11, 2001

(54) TRAINING METHOD AND APPARATUS FOR DENTAL BUR IDENTIFICATION

(75) Inventor: Larry Rose, Savannah, GA (US)

(73) Assignee: Brasseler USA 1 LP, Savannah, GA (US)

( * ) Notice: Subject to any disclaimer, the term of this patent is extended or adjusted under 35 U.S.C. 154(b) by 0 days.

(21) Appl. No.: 09/565,066

(22) Filed: May 5, 2000

Related U.S. Application Data

(60) Provisional application No. 60/156,518, filed on Sep. 29, 1999.

(51) Int. Cl.⁷ .................................................. A61G 15/00
(52) U.S. Cl. .............................. 433/77; 434/236; 206/369
(58) Field of Search ........................ 433/76, 77; 434/236, 434/237, 238; 206/369

(56) References Cited

U.S. PATENT DOCUMENTS

| | | |
|---|---|---|
| 1,043,891 | 11/1912 | Zange . |
| 3,817,588 * | 6/1974 | Helmers ............................ 312/209 |
| 4,397,395 | 8/1983 | McKelvey . |
| 4,448,307 * | 5/1984 | Roggenkamp ..................... 206/369 |
| 5,006,066 | 4/1991 | Rouse . |
| 5,108,287 | 4/1992 | Yee et al. . |
| 5,312,250 | 5/1994 | Ellman et al. . |
| 5,435,979 * | 7/1995 | Miller et al. ....................... 433/77 X |
| 5,525,314 * | 6/1996 | Hurson .............................. 433/77 X |

* cited by examiner

*Primary Examiner*—Nicholas D. Lucchesi
(74) *Attorney, Agent, or Firm*—Clark & Brody

(57) ABSTRACT

A bur block adapted for identifying and training dental personnel employs a block and a cover. The block has a surface having a number of holes sized to retain a number of dental burs. Each hole has indicia representing characteristics of the bur situated in the hole. The characteristics include sizes and shapes of the bur, colors, grits, part numbers, and the like. By putting the characteristics of each bur in proximity to the bur itself, persons can readily learn and/or become accustomed to the bur characteristics so that bur identification in the future is made easier.

21 Claims, 2 Drawing Sheets

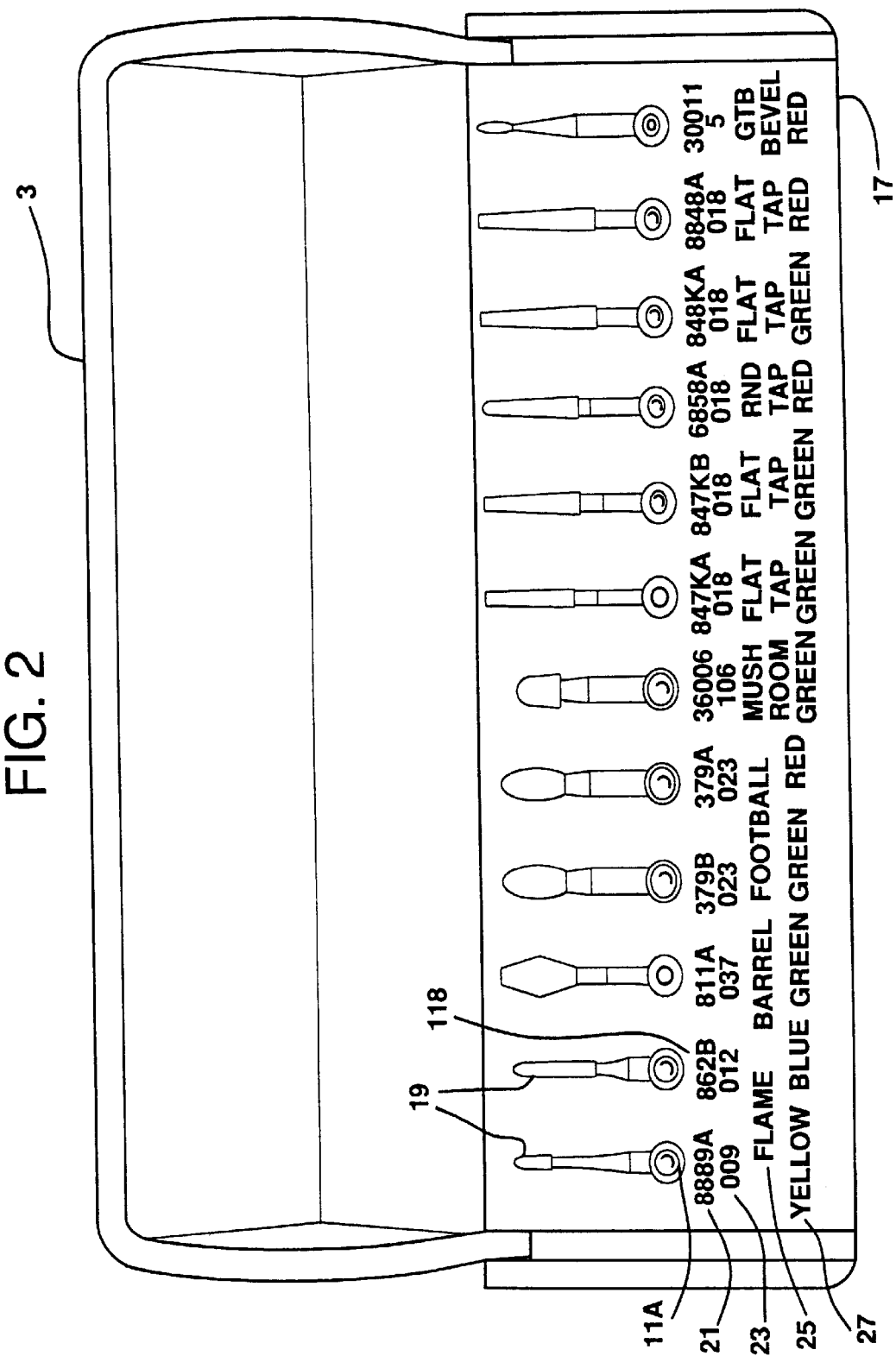

TRAINING METHOD AND APPARATUS FOR DENTAL BUR IDENTIFICATION

This application claims priority under 35 U.S.C. § 119(e) based on provisional patent application Ser. No. 60/156,518 filed on Sep. 29, 1999.

FIELD OF THE INVENTION

The present invention is directed to a method and apparatus for identifying dental burs, and one which teaches students or others to learn or identify bur characteristics such as bur shape, size, grit, and ordering information.

BACKGROUND ART

In the prior art, the use of blocks to retain dental burs is known. U.S. Pat. No. 5,108,287 to Yee et al. discloses an autoclavable drill bit container which relates to dental burs and/or drill bits which are to be placed in an autoclave. U.S. Pat. No. 4,397,395 to McKelvey discloses another dental bur holder which includes a member projecting generally upwardly from the holder body. The member has a smooth front surface which faces across an upper surface of the holder body. The two surfaces form a background which contrasts with the burs and against which the burs are viewed. The background is continuously color contrasting and is substantially visually uninterrupted except for the bur receiving apertures. This structure allows quick and accurate selection of the desired burs silhouetted against the contrasting background and also makes the problem of detecting damaged or imperfect burs easier.

However, a problem still exists in the field of containers holding dental burs. Often times, in dental schools, the dental bur holders are not adapted to easily identify the burs for proper placement and storage. As a result, many instruments are unnecessarily replaced or lost.

The invention overcomes the problems associated with prior art devices by providing a training system and apparatus which permits students and others such as central sterilization station personnel to visually identify bur order numbers, shapes and grits.

While the prior art teaches identifying drill bit sizes on drill bit holders, see U.S. Pat. No. 1,043,891 to Zange, this prior art does not teach or suggest an apparatus and method which effectively instructs students and others of the various characteristics associated with dental burs in a bur block.

SUMMARY OF THE INVENTION

Accordingly, it is a first object of the present invention to provide an improved method for training students and others in the use and identification of dental burs.

Another object of the present invention is a system or apparatus which allows a student or other person to readily identify a number of characteristics of a number of different dental burs.

A still further object of the present invention is to aid in the identification of the characteristics of dental burs in terms of bur shape, bur size, bur grit, bur ordering or part number information and the like.

Other objects and advantages of the present invention will become apparent as a description thereof proceeds.

In satisfaction of the foregoing objects and advantages, the present invention provides a method of training comprising providing a dental bur block holder which has recesses to store a number of different dental burs. The recesses are generally sized to receive the shanks or shafts of the burs. The recesses can be aligned in a row or another configuration so that the burs are easily accessible while being separated for ease of characteristic identification.

The block holder has a surface adjacent the recesses which includes a plurality of indicia associated with the respective bur in each recess. The indicia can be etched on the surface, inlaid, printed or the like. The indicia train a user of the block by identifying distinguishing characteristics of the burs. Thus, the student is better prepared in bur recognition when performing dental work. Characteristics include different surfaces and/or coatings such as tungsten carbide, diamond, and the like, bur head size, shaft diameter, the grit of the bur head, part numbers, illustrations of the bur shape, terms describing the bur shape such as football, flame, flat tap, etc., and the like.

In one embodiment, the recesses holding the bur shanks are aligned in a row to divide the top surface of the holder into front and rear sections. Preferably, the rear section has the illustration of the bur head and the front section has other indicia such as the bur size, bur part number, bur shape term, and bur grit color code.

BRIEF DESCRIPTION OF THE DRAWINGS

Reference is now made to the drawings of the invention wherein:

FIG. 2 shows a top view of the system of FIG. 2, enlarged to show greater detail.

DESCRIPTION OF THE PREFERRED EMBODIMENTS

Figure 1:
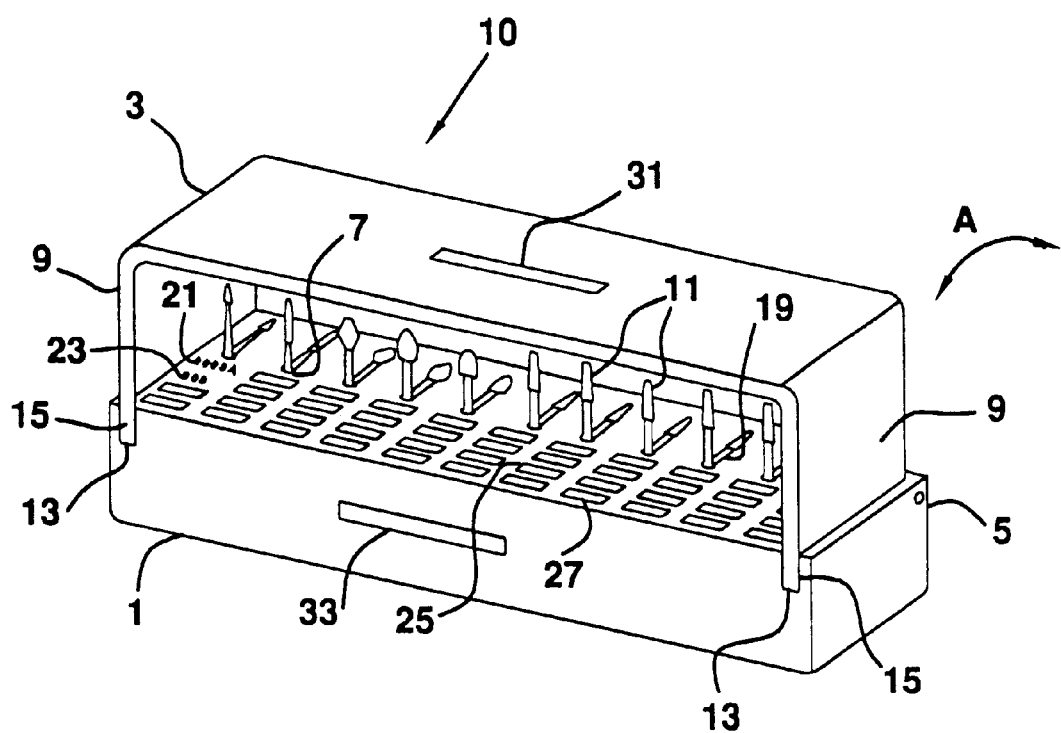
FIG. 1 shows a perspective view of an exemplary training system, including burs positioned in a bur block and training indicia.

The present invention offers significant improvements in the field of dentistry, particularly for training students and other personnel. When using the inventive apparatus and method, dental burs are more readily identified for training purposes as well as other purposes, e.g., sterilization, part ordering, etc.

FIG. 1 shows an exemplary apparatus of the invention designated by the reference numeral 10. The apparatus includes a block or a holder 1 and a cover 3. The block 1 is shown in a generally rectangular shape, but can have other shapes if desired. The cover 3 is designed to pivot about the pivot point 5, in the direction A as represented by the dual arrows. Other pivoting arrangements can be employed as would be within the skill of the art.

The block 1 has a plurality of recesses or openings 7, each recess 7 being sized to receive a portion of a bur 11, e.g., the bur shaft or shank. The cover 3 has side portions 9 which are preferably sized so that, when the cover 3 is in place, the burs 11 remain in the recesses 7 and cannot fall out even if the holder is tipped on its side or positioned in an upside down fashion. That is, the distance between an underside of the cover 3 and the bur distal end is less than the length of the bur proximal end resting in the recess 7. Thus, even if the block is inverted, each bur tip will strike the underside of the cover 3 rather than fall out of the recess 7.

In the FIG. 1 embodiment, the holder 1 has a pair of slots 13 which receive the free ends 15 of the side portions 9. The slots are sized to form a friction fit to keep the cover in a closed position. Of course, other locking mechanisms could be employed to keep the cover in the closed position.

With reference to FIGS. 1 and 2, the holder 1 is shown with a top surface 17. The top surface 17 has a number of indicia representing characteristics of the various burs 11. One set of indicia 19 illustrate the shape of the bur cutting head and a portion of the bur shaft. The indicia 19 are arranged in a row and are aligned with their respective burs.

Each of another set of indicia 21 identifies the bur in terms of a part number. Another set of indicia 23 identify each bur in terms of its size. For example, the two burs identified as 11A and 11B show sizes of "009" and "012". The values "009" and "012" represent the head size in millimeters.

Another set of indicia 25 identify the bur with a term representative of its shape. For example, burs 11A and 11B are characterized by the term "flame". Other burs are given other names such as barrel, football, mushroom tap, flat tap, and GTB bevel. Still other terms can be employed in association with each bur 11.

A still further set of indicia 27 associates a color with each bur. The 11A is represented by yellow with 11B represented by blue. The color indicia 27 typically represents a different diamond grit on each bur 11. For example, a green indicia can represent a coarse grit, e.g., 125 micron. A red indicia can represent a fine grit of about 30 micron.

Of course, other indicia may be used as part of the inventive training system and apparatus, e.g. bur shank size as a diameter.

With the inventive training apparatus, each bur is identified by a number of characteristics, not such bur size, thus permitting students or personnel in central sterilization stations to recognize burs and the indicia associated therewith. The blocks can come in various colors and configurations to meet different styles of burs, i.e., short shank, friction grip, right angle, and surgical or straight hand pieces. Because of the configuration of the cover 3, the instruments will not fall out of the block, no matter what the orientation of the block. The apparatus is also designed so that it can be autoclaved, particularly, dry heat autoclaved.

The indicia can be formed on the block in any known fashion such as etching, printing, inlaying or the like. The indicia should be formed as part of the block to withstand the conditions of sterilization of the block and instruments, e.g., autoclaving.

While the indicia are shown in rows in a particular order in FIG. 2, the ordering can be changed. For example, the indicia 19 could be switched with the indicia 21, 23, 25, and 27.

Indicia can also be placed on the top surface 31 of the cover 3 to associate a particular apparatus with a student or other user. Indicia 33 can be placed on the side of the holder 1 to identify a company, a supplier or other type of information.

Arranging the recesses 17 in a row divides the top surface 17 into front and rear sections. In this way, the front section can be employed for displaying indicia such as the bur part number, the bur size, terms indicating the bur shape, and terms showing grit characteristics, and the rear section can display an illustration of the bur shape. Positioning the illustration of the bur shape in the rear section of the top surface offers the added benefit of the illustration reinforcing a user's perspective view of the bur when extending from the recess 7.

As such, an invention has been disclosed in terms of preferred embodiments thereof which fulfills each and every one of the objects of the present invention as set forth above and provides new and improved training system and method for the identification of the characteristics of dental burs.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. A training method for identifying characteristics of dental burs comprising:
    a) providing a holder having a plurality of recesses, each recess sized to retain a dental bur, the holder having a surface adjacent the recesses; and
    b) displaying a plurality of indicia identifying each bur in each recess on the surface, the plurality of indicia representing a bur head illustration, and at least one of a bur head shape term, a bur surface grit, a bur size, and a bur part number for each recess.

2. The method of claim 1, further comprising displaying at least three indicia comprising the bur size, the bur head illustration, the bur head shape term, the bur surface grit, and the bur part number.

3. The method of claim 1, wherein the surface extends on either side of the recesses.

4. The method of claim 3, further comprising displaying at least three indicia comprising the bur size, the bur head illustration, the bur head shape term, the bur surface grit, and the bur part number on the surface.

5. The method of claim 1, further comprising arranging the plurality of recesses in a row so that the surface has front and rear sections and displaying the bur head illustration on the rear section and at least one of the bur size, the bur head shape term, the bur surface grit, and the bur part number on the front section.

6. The method of claim 1, wherein the bur head illustration shows a two dimensional representation of the bur head and a portion of a shank terminating with the bur head.

7. The method of claim 5, wherein the bur head illustration shows a two dimensional representation of the bur head and a portion of a bur shank terminating at the bur head.

8. The method of claim 1, comprising retaining each bur in each respective recess regardless of holder orientation by providing a cover adjacent a distal end of each bur, the cover being pivotal to allow access to each bur in an open position but performing the retaining step when in a closed position.

9. The method of claim 8, wherein each recess is sized to allow free movement of the bur up against the cover.

10. The method of claim 1, further comprising displaying each of the bur size, a bur head illustration, a bur head shape term, a bur surface grit, and a bur part number for each recess on the surface of the holder.

11. A training system comprising:
    a) a holder having a plurality of recesses, each recess sized to retain a dental bur, the holder having a surface adjacent the recesses and a cover to retain each bur in a respective recess; and
    b) a plurality of indicia displayed on the surface associated with each recess, the plurality of indicia including a bur head illustration, and at least one of a bur head shape term, a bur surface grit, a bur size, and a bur part number.

12. The system of claim 11, wherein the holder is autoclavable.

13. The system of claim 11, wherein the holder has a handle, the handle pivotally mounted to the holder.

14. The system of claim 13, wherein the handle is u-shaped and the holder has slots to receive free ends of the u-shaped handle.

15. The system of claim 11, wherein the plurality of indicia comprise each of the bur size, the bur head illustration, the bur head shape term, the bur part number, and the bur surface grit.

16. The system of claim 11, wherein the holder has a top and bottom surface and the plurality of recesses are arranged in a row in the top surface, the top surface divided into front and rear sections by the row, indicia representing a bur head illustration located on the rear section, and indicia representing at least one of the bur size, the bur head illustration, the bur head shape term, the bur part number, and the bur surface grit.

17. The system of claim 11, wherein each recess is sized to expose a bur length including a shank portion and a bur head of a bur disposed with the recess, and wherein the bur head illustration corresponds generally to the exposed bur length to facilitate identification of the bur length using the bur head illustration.

18. A training system comprising:
  a) a holder having a plurality of recesses, each recess sized to retain a dental bur, the recesses arranged in a row in a top surface of the holder;
  b) a u-shaped cover pivotally attached to the holder for movement between an open and a closed position, and being sized to retain each bur in a respective recess when in the closed position; and
  a plurality of indicia associated with each recess displayed on the top surface, the plurality of indicia including at least a bur head illustration, and one of a bur head shape term, a bur size, and a bur surface grit, each bur head illustration arranged along one side of the row with the remaining indicia arranged along the other side of the row.

19. The training system of claim 18, further comprising a bur part number indicia arranged along the other side.

20. The training system of claim 18, wherein each recess is sized to expose a bur length including a shank portion and a bur head of a bur disposed with the recess, and wherein the bur head illustration corresponds generally to the exposed bur length to facilitate identification of the bur length using the bur head illustration.

21. The system of claim 18, wherein each recess is sized to allow free movement of the bur up against the cover.

\* \* \* \* \*